US007850629B2

(12) United States Patent
Ravikumar

(10) Patent No.: US 7,850,629 B2
(45) Date of Patent: Dec. 14, 2010

(54) COMPRESSION APPARATUS FOR APPLYING LOCALIZED PRESSURE TO AN EXTREMITY

(76) Inventor: Sundaram Ravikumar, 265 Hardscrabble Rd., Briarcliff Manor, NY (US) 10510

( * ) Notice: Subject to any disclaimer, the term of this patent is extended or adjusted under 35 U.S.C. 154(b) by 1334 days.

(21) Appl. No.: 11/120,057

(22) Filed: May 2, 2005

(65) Prior Publication Data

US 2006/0247564 A1 Nov. 2, 2006

(51) Int. Cl.
*A61F 5/00* (2006.01)

(52) U.S. Cl. .......................................... 602/13; 602/5

(58) Field of Classification Search ......... 601/148–152; 602/1, 13, 14, 79, 75, 54–57, 60–65, 5; 606/201–202
See application file for complete search history.

(56) References Cited

U.S. PATENT DOCUMENTS 3,452,744 A * 7/1969 Van Den Nieuwenhof et al. .......................... 600/496
3,713,446 A * 1/1973 Sarnoff ....................... 606/202
4,289,106 A * 9/1981 Parietti ....................... 123/527
5,505,080 A * 4/1996 McGhee .................... 73/146.5
5,954,676 A 9/1999 Kramer, III
5,957,872 A 9/1999 Flick
6,247,497 B1 6/2001 Hirata et al.
6,852,089 B2 2/2005 Kloecker et al.
2003/0208848 A1* 11/2003 Flick et al. ..................... 5/713

* cited by examiner

*Primary Examiner*—Kim M Lewis
(74) *Attorney, Agent, or Firm*—Gordon & Jacobson, PC

(57) ABSTRACT

An apparatus for applying compression therapy to a portion of the human body includes a flexible member and an air bladder chamber. The flexible member is adapted to wrap around the body portion to secure the air bladder chamber thereto. An air pump inflates the air bladder chamber to a pressurized state. An adjustable pressure regulator is fluidly coupled to the bladder chamber and automatically limits the pressure to a selected amount. The pressure regulator preferably includes a plurality of check valves, each being operable at a different pressure and a selector element. The check valves are fluidly coupled to the selector and the selector is fluidly coupled to the bladder chamber. Operation of the selector fluidly couples one of the check valves to the bladder chamber. According to the presently preferred embodiment, three check valves are provided, operable at 20 mmHg, 30 mmHg, and 40 mmHg.

5 Claims, 4 Drawing Sheets

COMPRESSION APPARATUS FOR APPLYING LOCALIZED PRESSURE TO AN EXTREMITY

CROSS-REFERENCE TO RELATED APPLICATIONS

The present application is related to U.S. patent application Ser. No. 10/400,901, filed Mar. 27, 2003 and U.S. patent application Ser. No. 11/050,104 filed Jan. 24, 2005, the complete disclosures of which are hereby incorporated by reference herein.

BACKGROUND OF THE INVENTION

1. Field of the Invention

This invention relates to medical apparatus for applying pressure to an area of the human body in order to treat various conditions. More particularly, this invention relates to an inflatable apparatus which has a pressure selector which automatically regulates a selected inflation pressure.

2. State of the Art

A venous ulcer is a shallow wound (e.g., damage and loss of skin) that is the result of a problem with the veins in the leg. Venous ulcers typically develop on either side of the lower leg, above the ankle and below the calf. They are difficult to heal and often recur.

The veins of the leg are divided into the superficial and deep systems according to their position relative to the fascia. The deep veins, which come together to form the popliteal and femoral veins lie within the fascia and are responsible for the venous return from the leg muscles. Dilated valveless sinusoids also lie within the fascia (more particularly in the soleus and gastrocnemius muscles). The sinusoids fill with blood when the leg is at rest.

The major vessels of the superficial venous system are the long saphenous vein which runs along the medial side of the leg from foot to groin and the short saphenous vein which runs at the back of the calf from foot to knee. These vessels lie outside the fascia and are responsible for the venous return from the skin and subcutaneous fat.

Communicating veins, sometimes called perforators because they perforate the deep fascia, join the two systems. The perforators, like the other veins in the leg, contain valves that permit the flow of blood in one direction only, from the outer or superficial system inwards to the deep veins.

The venous pressure at the ankle of a subject who is lying supine is around 10 mmHg. Upon standing, the venous pressure will rise considerably due to an increase in hydrostatic pressure (equivalent to the weight of a vertical column of blood stretching from the point of measurement to the right auricle of the heart).

During walking, as the foot is dorsally flexed, the contraction of the calf muscle compresses the deep veins and soleal sinuses thereby emptying them of blood. As the foot is plantarly flexed, the pressure in the veins falls, the proximal valves close, and the veins are refilled by blood passing through the perforators from the superficial system. During this cycle, in a normal leg, the distal valves of the deep veins and the valves of the perforators will ensure that the expelled blood can go in only one direction—upwards, back to the heart.

Blockage or damage to the venous system will cause disruption to normal blood flow, which may manifest itself in a number of different ways according to the site and extent of the damage. If the valves in the superficial system are affected, venous return will be impaired and blood may accumulate in the veins causing them to become distended, leading to the formation of varicosities (varicose veins). If the function of the perforator valves is impaired, the action of the calf muscle pump will tend to cause blood to flow in the reverse direction into the superficial system increasing the possibility of damage to the superficial vessels.

Following a deep vein thrombosis that results in complete or partial obstruction of a deep vein, the unrelieved pressure produced by the calf muscle pump on the perforator valves may cause these to become incompetent. If this occurs, there will be a large rise in the pressure in the superficial system, which may force proteins and red cells out of the capillaries and into the surrounding tissue. Here, the red cells break down releasing a red pigment that causes staining of the skin, an early indicator of possible ulcer formation.

Venous leg ulcers are generally shallow and red in color. The skin surrounding the ulcer is frequently discolored due to the staining described previously. Incompetent perforating vein valves can also cause malleolar venules to become dilated and appear as fine red threads around the ankle. This condition, called ankle flair, is also diagnostic of a venous ulcer.

For patients with venous disease, the application of external compression can help to minimize or reverse the skin and vascular changes described previously, by forcing fluid from the interstitial spaces back into the vascular and lymphatic compartments. As the pressure within the veins of a standing subject is largely hydrostatic, it follows that the level of external pressure that is necessary to counteract this effect will reduce progressively up the leg, as the hydrostatic head is effectively reduced. For this reason it is usual to ensure that external compression is applied in a graduated fashion, with the highest pressure at the ankle. The preferred value for the degree of pressure varies according to a number of factors, including the severity of the condition and the height and limb size of the patient.

Medical hosiery represents a useful and convenient method of applying compression to normal shaped legs in order to prevent the development or recurrence of leg ulcers. However, these stockings are of limited value in the treatment of active ulceration, being difficult to apply over dressings. In such situations compression bandages currently represent the treatment of choice. Compression bandages apply a pressure to the limb that is directly proportional to bandage tension but inversely proportional to the radius of curvature of the limb to which it is applied. This means, therefore, that a bandage applied with constant tension to a limb of normal proportions will automatically produce graduated compression with the highest pressure at the ankle. This pressure will gradually reduce up the leg as the circumference increases.

As can be readily appreciated, it is cumbersome and difficult to apply uniform tension to the compression bandage as it is applied to the treated limb, and thus this is accomplished only by highly skilled caregivers. Moreover, once secured to the treated limb, care and attention must be given to ensure that the bandage does not slip or become displaced as this will lead to multiple layers forming, which in turn may lead to localized areas of high pressure, which can place the patient in direct risk of skin necrosis.

Mechanical compression treatments have also been proposed. An exemplary compression device is described in U.S. Pat. No. 5,031,604 to Dye. As generally described at col. 2, lines 33 et seq., an arrangement of chambers are provided that circumscribe the leg. An active pneumatic control system controls the pressure in the chambers to squeeze the leg near the ankle and then squeeze sequentially upward toward the knee in order to move blood from the extremity toward the heart. As noted in col. 4, lines 20-59 of U.S. Pat. No. 6,488,643 to Tumey et al., the mechanically produced compression levels may produce ischaemic (i.e., localized tissue anemia) not noted at similar compression levels obtained through bandaging. It may also produce cuffing (i.e., a reduction in leg pulsatile blood flow). The pneumatic control system is also bulky and heavy, which severely limits the mobility of the patient during treatment. Moreover, the pneumatic control system fails to provide a mechanism to ensure that excessive pressure, which can cause necrosis, is not applied to the treated limb. These limitations have resulted in most mechanical compression devices being contraindicated for patients exhibiting deep-vein thrombosis. Consequently, those skilled in the art have to date avoided such mechanical compression devices for the treatment of venous ulcers or edema of the extremities.

Thus, there are many problems, obstacles and challenges associated with the current treatments of leg ulcers and there is a need in the art to provide an apparatus for the treatment of venous ulcers (or an adema or other wound of the leg) that is simple to use, that is sure to produce the desired treatment, and that does not severely limit the mobility of the patient.

Previously incorporated application Ser. No. 10/400,901 discloses a device for applying pressure to the human leg for use in conjunction with treatment of varicose veins. The device includes a flexible member and at least one air bladder chamber integral thereto that are adapted to securely wrap around the human leg. A tube in fluid communication with the air bladder chamber(s) extends to an air pumping mechanism that operates to inflate the air bladder chamber(s) to a pressurized state. The flexible member preferably includes an opening at the knee joint level to enable a patella to protrude therethrough. In addition, the flexible member preferably extends below knee joint level and is adapted to securely wrap around a lower portion of a leg to provide stability to the leg. Preferably, the air bladder chamber of the device is substantially longer in a first dimension than in a second dimension orthogonal thereto such that the air bladder chamber can be positioned to cover a portion of the human leg that is relatively long in the vertical dimension and narrow in the horizontal dimension.

Previously incorporated application Ser. No. 11/050,104 discloses an apparatus for applying compression therapy to an extremity of the human body, such as a portion of the human leg. The device includes a flexible member and an air bladder chamber. The flexible member is adapted to wrap around the extremity to secure the air bladder chamber to the extremity. An air pumping mechanism is operated to inflate the air bladder chamber to a pressurized state. One or more fluid-filled pressurized members are provided, each separate and distinct from the flexible member and the air bladder chamber and thus readily moveable relative to the flexible member and the air bladder chamber. The pressurized member(s) is operably disposed between the extremity and the flexible member whereby it applies increased localized pressure to the extremity during use. Preferably, the air bladder chamber is substantially longer in a first dimension than in a second dimension orthogonal thereto such that it can extend longitudinally along the extremity to cover a relatively long and narrow portion of the extremity. The position of the air chamber can be readily adapted to apply local pressure to desired body parts (such as a certain venous channel). The pressurized member(s) can be positioned during use such that it covers a venous ulcer (or other treatment sites) and applies increased localized pressure to the treatment site in order to promote healing.

Depending on the severity of the condition being treated, more or less pressure is desirable. For this reason, the apparatus described in both of the parent applications have pressure gauges. However, in order to assure that the proper amount of pressure is applied, the practitioner must carefully observe the pressure gauge and stop inflating the bladder when the correct pressure has been reached. If the bladder is accidentally over inflated, the practitioner must release some air while watching the pressure gauge again.

SUMMARY OF THE INVENTION

It is therefore an object of the invention to provide an apparatus for compression therapy that is easy to use and provides accurate and adjustable control over the pressure applied to the treated areas of a human limb.

It is another object of the invention to provide such an apparatus that automatically regulates pressure to a selected amount.

In accord with these objects, which will be discussed in detail below, an apparatus is provided for applying compression therapy to a portion of the human body. The device includes a flexible member and an air bladder chamber. The flexible member is adapted to wrap around the body portion to secure the air bladder chamber to the body portion. An air pumping mechanism is operated to inflate the air bladder chamber to a pressurized state. An adjustable pressure regulator is fluidly coupled to the bladder chamber and automatically limits the pressure to a selected amount. According to the presently preferred embodiment, the pressure regulator includes a plurality of check valves, each being operable at a different pressure and a selector valve. The check valves are fluidly coupled to the selector valve and the selector valve is fluidly coupled to the bladder chamber. Operation of the selector valve fluidly couples one of the check valves to the bladder chamber. According to the presently preferred embodiment, three check valves operable at 20 mmHg, 30 mmHg, and 40 mmHg, respectively are provided.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
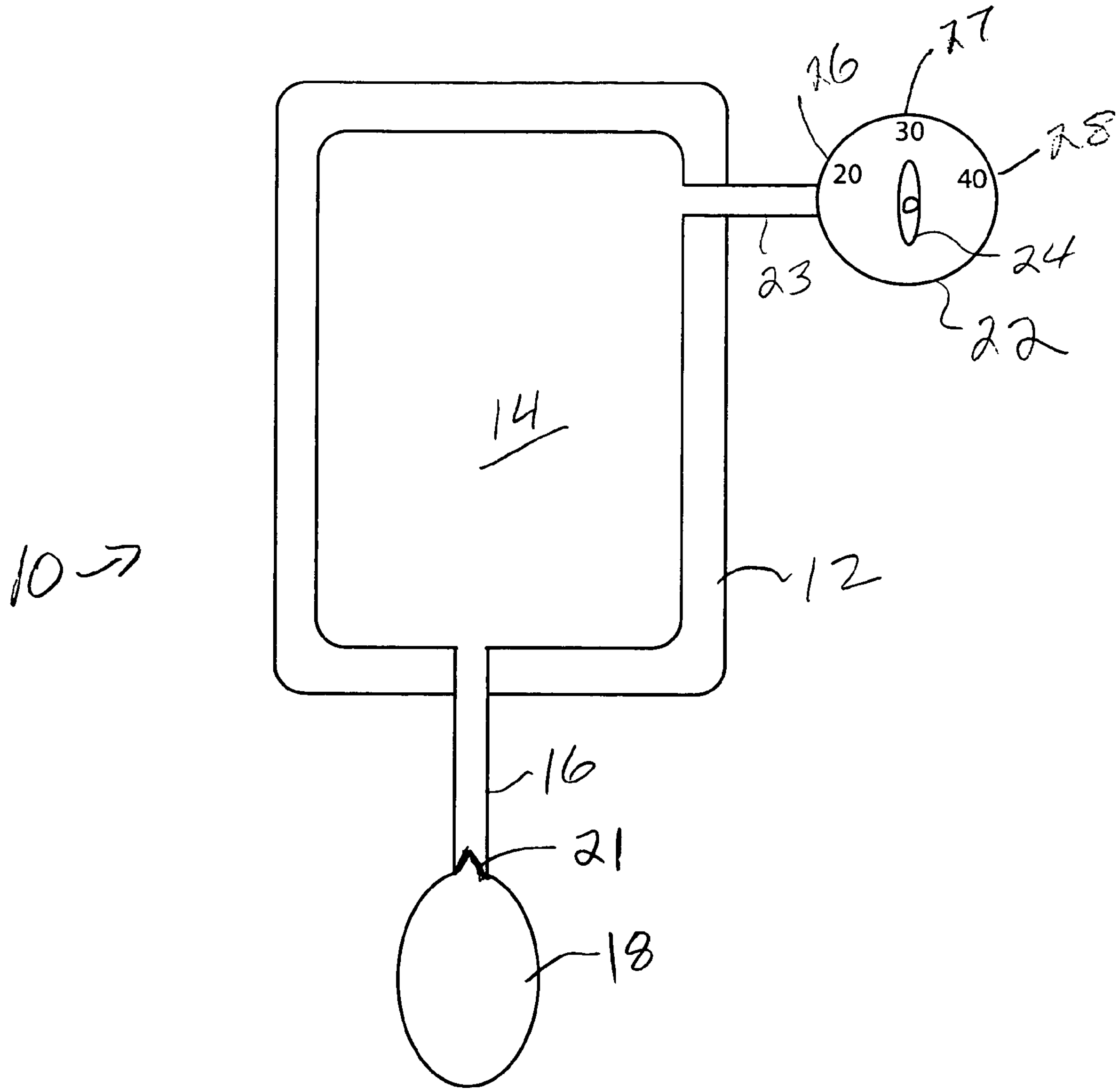
FIG. 1 is a schematic view of a compression apparatus according to the invention.

Turning now to FIG. 1, a pneumatic compression mechanism is provided for applying pressure to part of the human body. The pneumatic compression mechanism 10 includes a flexible member 12 and one or more inflatable air bladder chambers 14 (preferably, a single air bladder as shown). The inflatable air bladder chamber 14 is preferably secured to the flexible member 12 in its unwrapped state. For example, the flexible member 12 may comprise two layers of elastomeric material with the air bladder chamber(s) 14 affixed between these two layers by nylon threads or other suitable fastening means. Alternatively, the flexible member 12 may include pockets into which the air bladder chamber(s) 14 are removably inserted and securely held therein. In yet another alternative embodiment, the air bladder may be glued or welded to the inside surface of the member 12. The elastomeric material of the member 12 may be realized from nylon, polyurethane, cotton, or other suitable material. A tube 16, which is in fluid communication with the air bladder chamber(s) 14, extends to a pumping bulb 18. The pumping bulb 18, which is preferably made of rubber, includes a one-way valve 21 that regulates the pumping of air into the air bladder chamber(s) 14 via the tube 16. Air is pumped into the air bladder chamber(s) 14 by squeezing the pumping bulb 18. In this manner, the air bladder chamber(s) 14 are placed into a pressurized state.

An adjustable pressure regulator 22 is fluidly coupled to the bladder chamber 14 via a tube 23. The regulator 22 has a rotatable knob 24 which is rotatable to three positions 26, 27, 28, each corresponding to a different pressure which is indicated on the regulator with indicia. As illustrated, the first position 26 corresponds to a pressure of 20 mmHg, the second position 27 corresponds to a pressure of 30 mmHg, and the third position 28 corresponds to a pressure of 40 mmHg. For convenience of illustration, the pressure selector has been shown distant from the pumping bulb. It will be appreciated, however, that the pressure selector could be located adjacent the pumping bulb 18 and could even be coupled to the same tube 16 as the pumping bulb.

Figure 2:
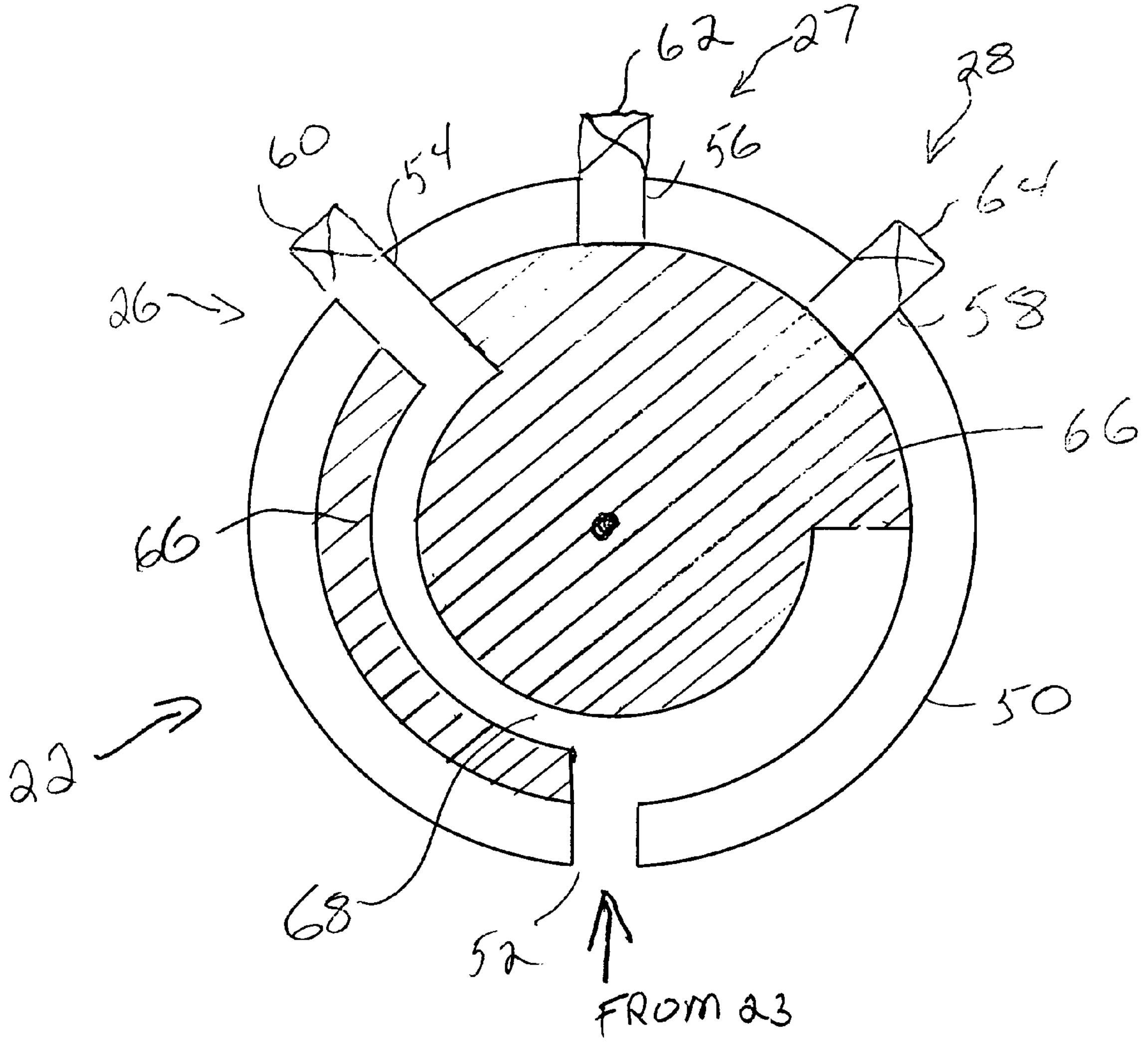
FIG. 2 is a schematic view of a selector valve in a first position fluidly coupling a first check valve to the bladder chamber of the compression apparatus.
Figure 3:
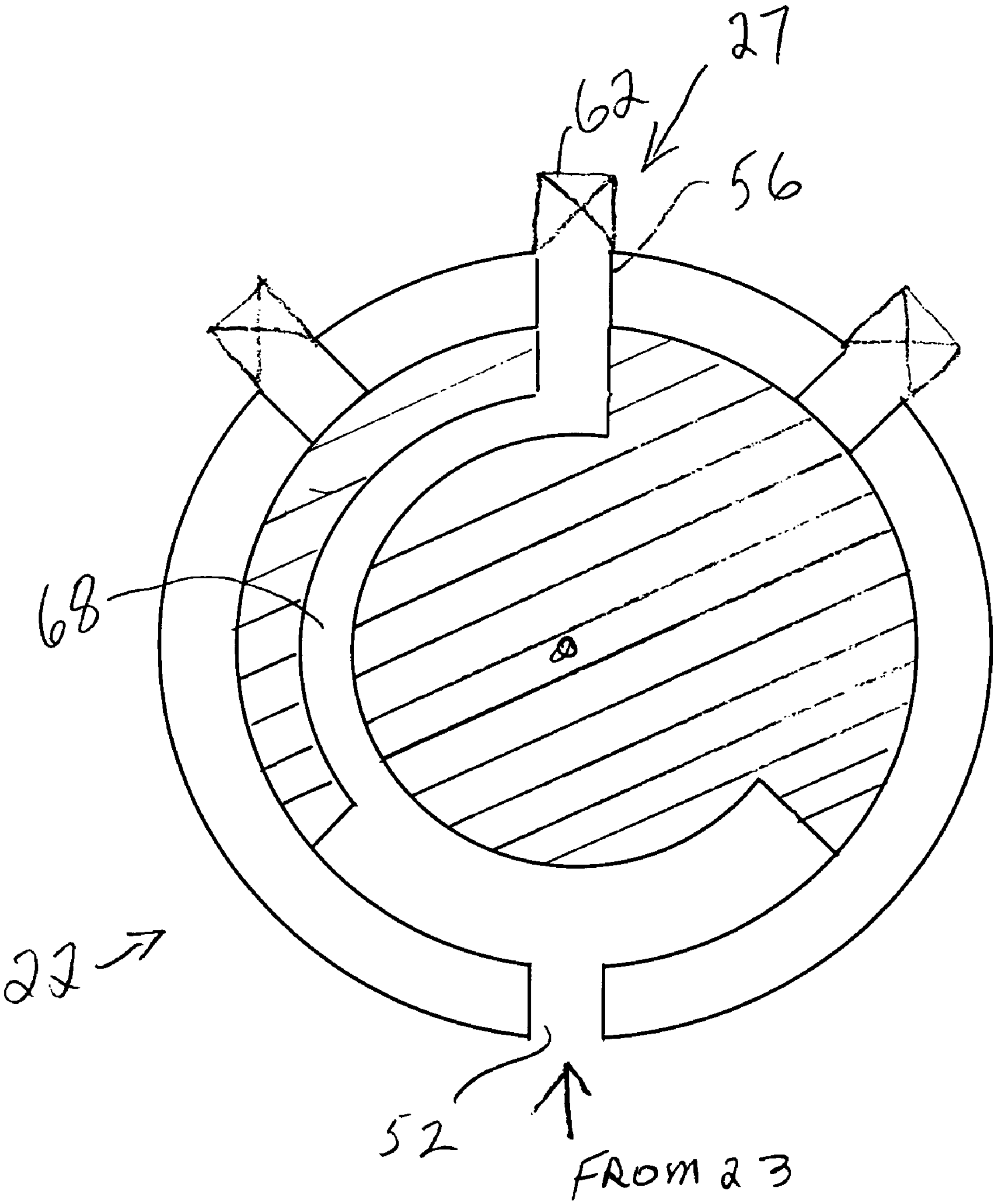
FIG. 3 is a schematic view of a selector valve in a second position fluidly coupling a second check valve to the bladder chamber of the compression apparatus.
Figure 4:
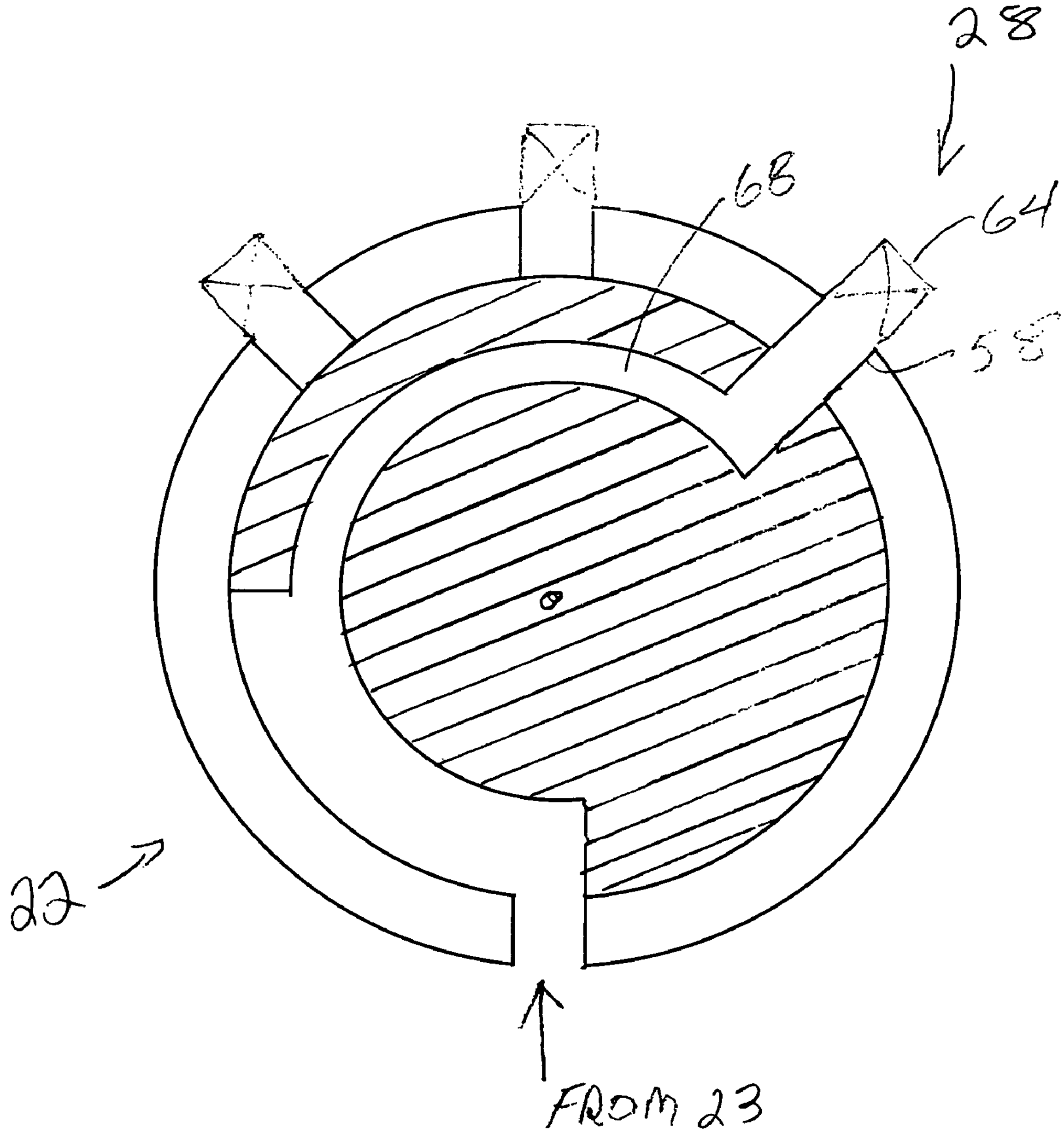
FIG. 4 is a schematic view of a selector valve in a third position fluidly coupling a third check valve to the bladder chamber of the compression apparatus.

FIGS. 2-4 illustrate an embodiment of a pressure regulator 22. The pressure regulator 22 includes a housing 50 having four fluid ports 52, 54, 56, 58. The fluid port 52 is coupled to the tube 23 (FIG. 1). The fluid port 54 is coupled to a first check valve 60 which is operable (i.e., opens) at a pressure of 20 mmHg. The fluid port 56 is coupled to a second check valve 62 which is operable (i.e., opens) at a pressure of 30 mmHg. The fluid port 58 is coupled to a third check valve 64 which is operable (i.e., opens) at a pressure of 40 mmHg. A rotatable gate 66 having a fluid channel 68 is disposed inside the housing 50 and is rotatable by the knob 24 (FIG. 1).

When the knob is rotated to the first position 26, the fluid channel 68 aligns with ports 52 and 54 (ports 56 and 58 being blocked) thereby fluidly coupling the bladder chamber 14 (FIG. 1) with the check valve 60 as shown in FIG. 2. When the bladder chamber is inflated, air flows through the pressure selector to the check valve 60. When pressure in the bladder exceeds 20 mmHg, the valve 60 opens allowing air to escape. When sufficient air has escaped to bring the pressure back to 20 mmHg, the valve 60 closes.

When the knob is rotated to the second position 27, the fluid channel 68 aligns with ports 52 and 56 (ports 54 and 58 being blocked) thereby fluidly coupling the bladder chamber 14 (FIG. 1) with the check valve 62 as shown in FIG. 3. When the bladder chamber is inflated, air flows through the pressure selector to the check valve 62. When pressure in the bladder exceeds 30 mmHg, the valve 62 opens allowing air to escape. When sufficient air has escaped to bring the pressure back to 30 mmHg, the valve 62 closes.

When the knob is rotated to the third position 28, the fluid channel 68 aligns with ports 52 and 58 (ports 54 and 56 being blocked) thereby fluidly coupling the bladder chamber 14 (FIG. 1) with the check valve 64 as shown in FIG. 4. When the bladder chamber is inflated, air flows through the pressure selector to the check valve 64. When pressure in the bladder exceeds 40 mmHg, the valve 64 opens allowing air to escape. When sufficient air has escaped to bring the pressure back to 40 mmHg, the valve 64 closes.

Referring now to the figures generally, from the foregoing description those skilled in the art will appreciate how to operate the compression apparatus. First the flexible member 12 is attached to a body part as described in the parent applications. Second, the desired pressure is selected by rotating the knob 24 (although this could be done before attaching the flexible member 12 to the body part). Third, the pumping bulb is squeezed until air is heard or felt to escape from the selected check valve. If desired, check valves having visual indicators can be used so that there is a visual indication of when the check valve opens.

There have been described and illustrated herein a preferred embodiment of an apparatus (and corresponding method of operation) that is secured to a portion of the human body and controlled to apply localized pressure. While a particular embodiment of the invention has been described, it is not intended that the invention be limited thereto, as it is intended that the invention be as broad in scope as the art will allow and that the specification be read likewise. Thus, while a particular selector valve been disclosed, it will be appreciated that other suitable selector valves (e.g. a ball valve) may be used. In addition, the air pump mechanism may include an automatic air pumping mechanism rather than a hand-held manually actuated air pumping mechanism as described above. In addition, the air pump mechanism may be removably coupled to the bladder. It will therefore be appreciated by those skilled in the art that yet other modifications could be made to the provided invention without deviating from its spirit and scope as claimed.

What is claimed is:

1. An apparatus for applying pressure to a portion of the human body comprising:

a) a flexible member and an air bladder chamber, wherein said flexible member is adapted to wrap around the portion of the human body to secure said air bladder chamber to the portion of the body;

b) an air pump operably coupled to said air bladder chamber, said air pump operating to inflate said air bladder chamber to a pressurized state; and c) an adjustable pressure regulator coupled to said air bladder chamber, said pressure regulator being selectively adjustable to prevent the pressure in the bladder chamber from exceeding a selected pressure from a plurality of predetermined pressures, wherein said pressure regulator includes a plurality of check valves, each being operable at a different pressure.

2. The apparatus according to claim 1, wherein:

said pressure regulator includes a selector element coupled to said check valves and to said bladder chamber, said selector element being adjustable to couple a selected one of said check valves to said bladder chamber.

3. The apparatus according to claim 2, wherein:

said plurality of check valves number three.

4. The apparatus according to claim 3, wherein:

said check valves are operable at 20 mmHg, 30 mmHg, and 40 mmHg, respectively.

5. The apparatus according to claim 1, wherein:

said adjustable pressure regulator includes a rotating member used to select said selected pressure from said plurality of predetermined pressures.

* * * * *